United States Patent [19]

Hamamura et al.

[11] Patent Number: 5,686,635
[45] Date of Patent: Nov. 11, 1997

[54] TETRAHYDRO-ALKENYL-METHANONAPHTHALENE-5,8-DIONE DERIVATIVES

[75] Inventors: Kimio Hamamura, Chiba Prefecture; Tetsuo Iwama, Ibaraki Prefecture; Chiaki Seki, Aichi Prefecture; Masayuki Konishi, Ibaraki Prefecture, all of Japan

[73] Assignee: Eisai Chemical Co., Ltd., Japan

[21] Appl. No.: 686,484

[22] Filed: Jul. 26, 1996

Related U.S. Application Data

[60] Continuation of Ser. No. 434,758, May 4, 1995, abandoned, which is a division of Ser. No. 203,372, Mar. 1, 1994, Pat. No. 5,476,955.

[30] Foreign Application Priority Data

Mar. 1, 1993 [JP] Japan .................................. 5-62463
Oct. 8, 1993 [JP] Japan ................................. 5-275914

[51] Int. Cl.$^6$ ........................................... C07C 50/04
[52] U.S. Cl. ............................ 552/293; 552/298; 552/299
[58] Field of Search ........................... 552/299, 293, 552/298

[56] References Cited

U.S. PATENT DOCUMENTS 4,853,156  8/1989  Ruttiman et al. ................. 552/299

Primary Examiner—Rebecca Cook
Attorney, Agent, or Firm—Wenderoth, Lind & Ponack

[57] ABSTRACT

Disclosed herein are a quinone derivative represented by the following formula:

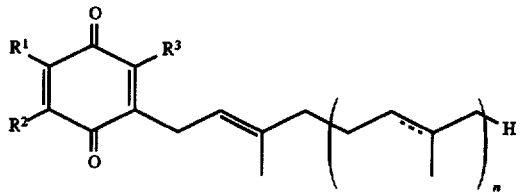

wherein $R^1$ and $R^2$ are identical with or different from each other and mean individually a lower alkyl or lower alkoxy group, or may form an aromatic ring together, $R^3$ denotes a lower alkyl group, n stands for 0 or an integer of 1–9, and a linkage --- is a single or double bond, such as a vitamin K derivative or coenzyme derivative; and a process for the preparation of the quinone derivative at a high yield without forming any geometric isomer; as well as a $1,4,4_a,8_a$-tetrahydro-$4_a\alpha$-alkenyl-$1\alpha,4\alpha$-methanonaphthalene-5,8-dione derivative which is useful as an intermediate for the preparation of the quinone derivative.

2 Claims, No Drawings

TETRAHYDRO-ALKENYL-METHANONAPHTHALENE-5,8-DIONE DERIVATIVES

This application is a continuation of now abandoned application, Ser. No. 08/434,758, filed May 4, 1995, now abandoned, which is a divisional of Ser. No. 08/203,372, filed Mar. 1, 1994, now U.S. Pat. No. 5,476,955, issued Dec. 19, 1995.

BACKGROUND OF THE INVENTION

1. Field of the Invention

The present invention relates to new industrial processes for the preparation of vitamin K derivatives, which play an important role in the vital body as hematostatic vitamins, coenzyme Q derivatives, which are useful as therapeutic agents for ischemic heart diseases such as congestive heart failure, and the like, and intermediates useful for the preparation thereof.

2. Description of the Background Art

It has heretofore been known that quinone derivatives can be prepared by reacting 2-methyl-1,4-naphthoquinone (common name: menadione; in the following chemical reaction formula, $R^1$ and $R^2$ form a benzene ring), 2,3-dimethoxy-5-methylbenzoquinone (in the following chemical reaction formula, $R^1 = R^2$ = a methoxy group), or the like with an allyl halide derivative in accordance with the Friedel-Crafts reaction as shown by the following chemical reaction formula:

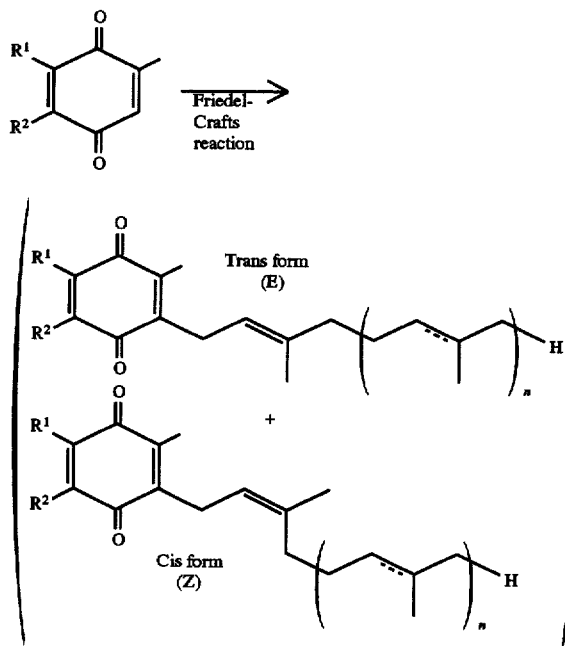

wherein $R^1$ and $R^2$ are identical with or different from each other and mean individually a lower alkyl or lower alkoxy group, or may form an aromatic ring together, n stands for 0 or an integer of 1–9, and a linkage --- is a single or double bond.

Besides, Japanese Patent Application Laid-Open (KOKAI) No. 56935/1985 discloses a process for preparing a quinone derivative by forming 1,4,4$_a$α,9$_a$-tetrahydro-9$_a$α-methyl-1α,4α-methanoanthraquinone from 2-methyl-1,4-naphthoquinone and cyclopentadiene, reacting this product with an allyl halide derivative into a 1,4,4$_a$α,9$_a$-tetrahydro-9$_a$α-methyl-4$_a$α-alkenyl-1α,4α-methanoanthraquinone, and then subjecting the thus-obtained product to a Retro Diels-Alder reaction.

In the conventional processes for preparing quinone derivatives, 2-methyl-1,4-naphthoquinone, 2,3-dimethoxy-5-methylbenzoquinone or the like has been used as a starting material as shown in the above chemical reaction formula. However, these compounds have been extremely expensive and hence difficult to obtain in a great amount on an industrial scale. Further, quinone derivatives produced by conducting the Friedel-Crafts reaction undergo geometric isomerization on the allyl group. Therefore, the final product is provided as a mixture of cis (Z) and trans (E) isomers. In addition, they are very difficult to separate from each other to purify them because their physicochemical properties are similar to each other. Accordingly, this process has not been said to be an industrially or economically satisfactory process.

On the other hand, the process disclosed in Japanese Patent Application Laid-Open (KOKAI) No. 56935/1985 can improve the disadvantage that the geometric isomers are formed, but has remained using 2-methyl-1,4-naphthoquinone as a starting material. Therefore, a problem has remained unsolved from the viewpoint of obtaining the starting material.

In addition, the process disclosed in Japanese Patent Application Laid-Open (KOKAI) No. 56935/1985 requires a strong base such as a metal amide, lithium dialkylamide or alkali metal t-butyrate for the reaction of 1,4,4$_a$α,9$_a$-tetrahydro-9$_a$α-methyl-1α,4α-methanoanthraquinone or the like with an allyl halide derivative. However, these strong bases are materials difficult to industrially handle in a great amount from the viewpoint of flammability, corrosiveness, decomposition behavior due to moisture absorption, toxicity, shelf stability and the like.

1,4,4$_a$α,9$_a$-Tetrahydro-9$_a$α-methyl-1α,4α-methanoanthraquinone or the like, which is a starting material in the above publication, is obtained by the Diels-Alder reaction of 2-methyl-1,4-naphthoquinone, 2,3-dimethoxy-5-methylbenzoquinone or the like with cyclopentadiene. However, this addition reaction is greatly affected by the steric hindrance of the methyl group attached to an α position of the quinone. Therefore, the reaction is extremely slow, and it takes four long days to complete the reaction as described in Examples of the above publication. Such a process has hence been disadvantageous from the industrial viewpoint.

As described above, the disadvantage of forming the geometric isomers, the problem from the viewpoint of obtaining starting materials, the difficulty of handling the bases, or the time problem involved in the preparation of the starting material has not been yet solved in the conventionally-known processes. Therefore, such processes all have been insufficient for industrial process. With such a background, there has been demand for development of an industrially excellent preparation process for quinone derivatives, by which an intended quinone derivative can be prepared from cheap and easily available starting materials with good operating simplicity for a short period of time without forming any geometric isomer.

SUMMARY OF THE INVENTION

Therefore, the present inventors have carried out an extensive investigation with a view toward improving the above-described problems involved in the conventionally-known processes. As a result, it has been found that when a cheap and easily available 1,4-naphthoquinone, 1,4- benzoquinone or the like is used as a starting material to react it with cyclopentadiene into a 1,4,4$_a$,8$_a$-tetrahydro-1α, 4α-methanonaphthalene-5,8-dione derivative (IV), the derivative (IV) is reacted with an allyl derivative (V) into a 1,4,4$_a$,8$_a$-tetrahydro-4$_a$α-alkenyl-1α,4α-methanonaphthalene-5,8-dione derivative (I), the derivative (I) is reacted with an alkyl halide (R$^3$X) into a 1,4,4$_a$,8$_a$-tetrahydro-4$_a$α-alkenyl-8$_a$α-alkyl-1α,4α-methanonaphthalene-5,8-dione derivative (II), and the derivative (II) is then subjected to a Retro Diels-Alder reaction, or the 1,4,4$_a$,8$_a$-tetrahydro-4$_a$α-alkenyl-1α,4α-methanonaphthalene-5,8-dione derivative (I) is subjected to a Retro Diels-Alder reaction, a quinone derivative (III) or (VI), which will be described subsequently, can be industrially prepared at a high yield without forming any geometric isomer while attaining the desired ends, thus leading to completion of the present invention. The outline of the reaction paths in the present invention is shown by the following chemical reaction formula:

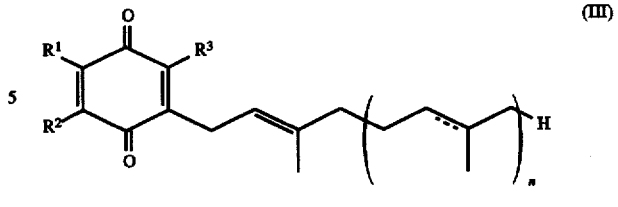

wherein R$^1$ and R$^2$ are identical with or different from each other and mean individually a lower alkyl or lower alkoxy group, or may form an aromatic ring together, R$^3$ denotes a lower alkyl group, n stands for 0 or an integer of 1–9, and a linkage $=\!=\!=$ is a single or double bond, which comprises reacting a 1,4,4$_a$,8$_a$-tetrahydro-4$_a$α-alkenyl-1α,4α-methanonaphthalene-5,8-dione derivative represented by the following formula (I):

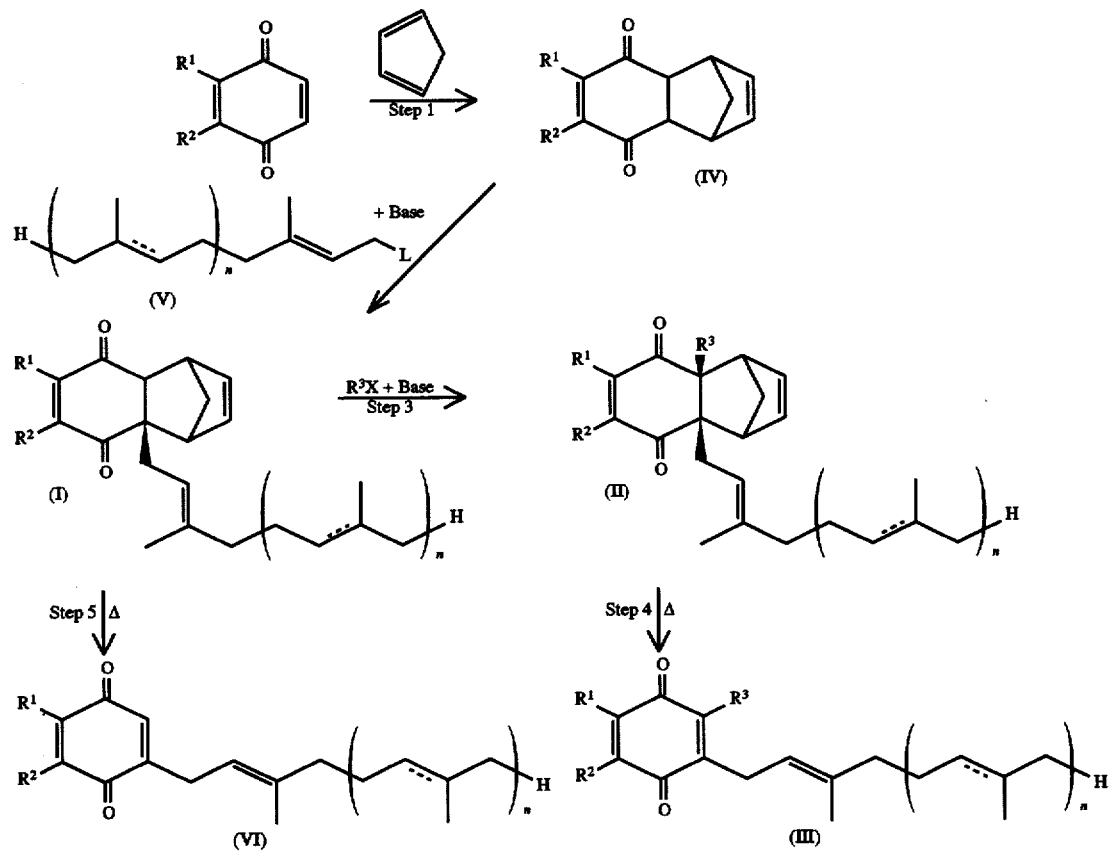

It is therefore an object of the present invention to provide industrially excellent processes for preparing vitamin K derivatives, which play an important role in the vital body as hematostatic vitamins, coenzyme Q derivatives, which are useful as therapeutic agents for ischemic heart diseases such as congestive heart failure, and the like, and intermediates useful for the preparation thereof.

In an aspect of the present invention, there is thus provided a process for the preparation of a quinone derivative represented by the following formula (III):

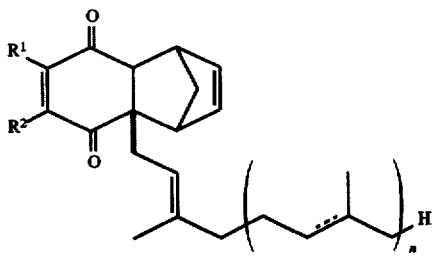

wherein $R^1$, $R^2$, n and a linkage $\rlap{-}=$ have the same meaning as defined above, with an alkyl halide represented by the following formula:

R³X wherein $R^3$ has the same meaning as defined above, and X denotes a halogen atom, in the presence of a base to form a $1,4,4_a,8_a$-tetrahydro-$4_a\alpha$-alkenyl-$8_a\alpha$-alkyl-$1\alpha,4\alpha$-methanonaphthalene-5,8-dione derivative represented by the following formula (II):

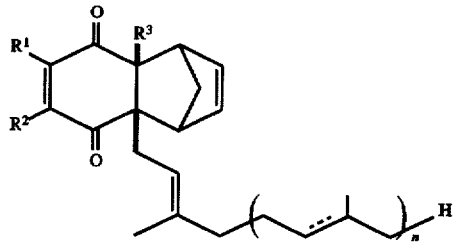

wherein $R^1$, $R^2$, $R^3$, n and a linkage $\rlap{-}=$ have the same meaning as defined above, and then subjecting the thus-formed derivative (II) to a Retro Diels-Alder reaction.

In another aspect of the present invention, there is also provided a process for the preparation of a quinone derivative represented by the formula (III), which comprises reacting a $1,4,4_a,8_a$-tetrahydro-$1\alpha,4\alpha$-methanonaphthalene-5,8-dione derivative represented by the following formula (IV):

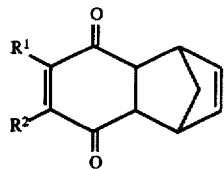

wherein $R^1$ and $R^2$ have the same meaning as defined above, with an allyl derivative represented by the following formula (V):

wherein L means a halogen atom, alkylsulfonyl group or arylsulfonyl group, and n and a linkage $\rlap{-}=$ have the same meaning as defined above, in the presence of a base to form a $1,4,4_a,8_a$-tetrahydro-$4_a\alpha$-alkenyl-$1\alpha,4\alpha$-methanonaphthalene-5,8-dione derivative represented by the formula (I), reacting the thus-formed derivative (I) with an alkyl halide represented by the following formula:

R³X in the presence of a base to form a $1,4,4_a,8_a$-tetrahydro-$4_a\alpha$-alkenyl-$8_a\alpha$-alkyl-$1\alpha,4\alpha$-methanonaphthalene-5,8-dione derivative represented by the formula (II), and then subjecting the thus-formed derivative (II) to a Retro Diels-Alder reaction.

In a further aspect of the present invention, there is provided a process for the preparation of a quinone derivative represented by the following formula (VI):

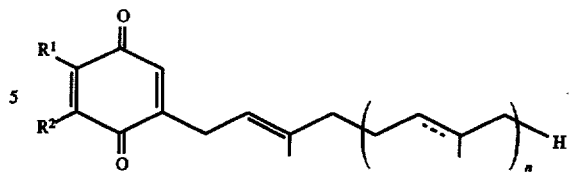

wherein $R^1$, $R^2$, n and a linkage $\rlap{-}=$ have the same meaning as defined above, which comprises subjecting a $1,4,4_a,8_a$-tetrahydro-$4_a\alpha$-alkenyl-$1\alpha,4\alpha$-methanonaphthalene-5,8-dione derivative represented by the formula (I) to a Retro Diels-Alder reaction.

In a still further aspect of the present invention, there is provided a process for the preparation of a quinone derivative represented by the formula (VI), which comprises reacting a $1,4,4_a,8_a$-tetrahydro-$1\alpha,4\alpha$-methanonaphthalene-5,8-dione derivative represented by the formula (IV) with an allyl derivative represented by the formula (V) in the presence of a base to form a $1,4,4_a,8_a$-tetrahydro-$4_a\alpha$-alkenyl-$1\alpha,4\alpha$-methanonaphthalene-5,8-dione derivative represented by the formula (I), and subjecting the thus-formed derivative (I) to a Retro Diels-Alder reaction.

In a yet still further aspect of the present invention, there is provided a $1,4,4_a,8_a$-tetrahydro-$4_a\alpha$-alkenyl-$1\alpha,4\alpha$-methano-naphthalene-5,8-dione derivative represented by the formula (I).

The above and other objects, features and advantages of the present invention will become apparent from the following description and the appended claims.

DETAILED DESCRIPTION OF THE INVENTION AND PREFERRED EMBODIMENTS

The $1,4,4_a,8_a$-tetrahydro-$1\alpha,4\alpha$-methanonaphthalene-5,8-dione derivatives useful in the practice of the present invention are represented by the following formula (IV):

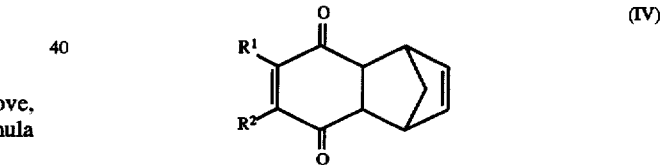

In the formula (IV), $R^1$ and $R^2$ are identical with or different from each other and mean individually a lower alkyl or lower alkoxy group. More specifically, examples of the lower alkyl group may include alkyl groups having 1–6 carbon atoms, such as methyl, ethyl, n-propyl, i-propyl, n-butyl, i-butyl, t-butyl, amyl and hexyl groups. Examples of the lower alkoxy group may include groups such as methoxy, ethoxy, n-propoxy, i-propoxy, n-butoxy, i-butoxy, t-butoxy, pentyloxy and hexyloxy groups, in which an oxygen atom is bonded to the respective lower alkyl group mentioned above. The methoxy group is particularly preferred. $R^1$ and $R^2$ may form an aromatic ring together. Specific examples of the $1,4,4_a,8_a$-tetrahydro-$1\alpha,4\alpha$-methanonaphthalene-5,8-dione derivatives (IV) may include the following compounds though they are not limited to such compounds in the present invention.

(1) $1,4,4_a,9_a$-Tetrahydro-$1\alpha,4\alpha$-methanoanthraquinone; and (2) $1,4,4_a,8_a$-Tetrahydro-6,7-dimethoxy-$1\alpha,4\alpha$-methanonaphthalene-5,8-dione.

The allyl derivatives useful in the practice of the present invention are represented by the following formula (V):

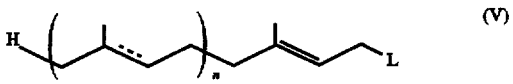
(V)

In the formula (V), L means a halogen atom, alkylsulfonyl group or arylsulfonyl group. Specific examples of the halogen atom may include bromine, iodine, chlorine and fluorine atoms. Specific examples of the alkylsulfonyl group may include methanesulfonyl and ethanesulfonyl groups, and the like. Specific examples of the arylsulfonyl group may include benzenesulfonyl and toluenesulfonyl groups, and the like. n stands for 0 or an integer of 1–9, and a linkage $=\!=\!=$ denotes a single or double bond. Various geometric isomers (E-Z isomers or cis-trans isomers) exist in the allyl derivatives (V). However, no limitation is imposed on such compounds, and any isomers may hence be used in the present invention.

Specific examples of the allyl derivatives (V) may include the following compounds though they are not limited to such compounds in the present invention.

(1) 3-Methyl-2-butenyl bromide;
(2) 3-Methyl-2-butenyl chloride;
(3) 3-Methyl-2-butenyl iodide;
(4) 3-Methyl-2-butenyl methanesulfonate;
(5) 3-Methyl-2-butenyl p-toluenesulfonate;
(6) Geranyl bromide;
(7) Farnesyl bromide;
(8) Geranylgeranyl bromide;
(9) Geranylfarnesyl bromide;
(10) Farnesylfarnesyl bromide;
(11) Solanesyl bromide; and
(12) Phytyl bromide.

The $1,4,4_a,8_a$-tetrahydro-$4_a\alpha$-alkenyl-$1\alpha,4\alpha$-methanonaphthalene-5,8-dione derivatives useful in the practice of the present invention are represented by the following formula (I):

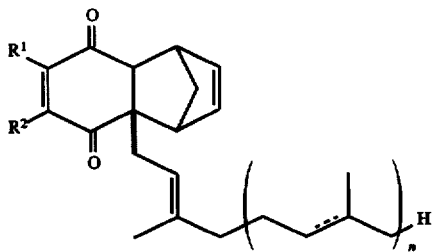
(I)

In the formula (I), $R^1$, $R^2$, n and a linkage $=\!=\!=$ have the same meaning as defined above. Specific examples of the $1,4,4_a,8_a$-tetrahydro-$4_a\alpha$-alkenyl-$1\alpha,4\alpha$-methanonaphthalene-5,8-dione derivatives (I) may include the following compounds though they are not limited to such compounds in the present invention.

(1) $1,4,4_a,9_a$-Tetrahydro-$4_a\alpha$-(3'-methyl-2'-butenyl)-$1\alpha,4\alpha$-methanoanthraquinone;
(2) $1,4,4_a,9_a$-Tetrahydro-$4_a\alpha$-(3',7'-dimethyl-2',6'-octadienyl)-$1\alpha,4\alpha$-methanoanthraquinone;
(3) $1,4,4_a,9_a$-Tetrahydro-$4_a\alpha$-(3',7',11'-trimethyl-2',6',10'-dodecatrienyl)-$1\alpha,4\alpha$-methanoanthraquinone;
(4) $1,4,4_a,9_a$-Tetrahydro-$4_a\alpha$-(3',7',11'-15'-tetramethyl-2',6',10',14'-hexadecatetraenyl)-$1\alpha,4\alpha$-methanoanthraquinone;
(5) $1,4,4_a,9_a$-Tetrahydro-$4_a\alpha$-(3',7',11',15',19'-pentamethyl-2',6',10',14',18'-eicosadecaheptaenyl)-$1\alpha,4\alpha$-methanoanthraquinone;
(6) $1,4,4_a,9_a$-Tetrahydro-$4_a\alpha$-(3',7',11',15'-tetramethyl-2'-hexadecaenyl)-$1\alpha,4\alpha$-methanoanthraquinone; and
(7) $1,4,4_a,8_a$-Tetrahydro-6,7-dimethoxy-$4_a\alpha$-solanesyl-$1\alpha,4\alpha$-methanonaphthalene-5,8-dione.

The $1,4,4_a,8_a$-tetrahydro-$4_a\alpha$-alkenyl-$8_a\alpha$-alkyl-$1\alpha,4\alpha$-methanonaphthalene-5,8-dione derivatives useful in the practice of the present invention are represented by the following formula (II):

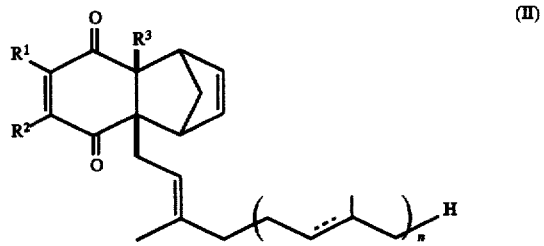
(II)

In the formula (II), $R^1$, $R^2$, n and a linkage $=\!=\!=$ have the same meaning as defined above, and $R^3$ means a lower alkyl group. More specifically, examples of the lower alkyl group may include alkyl groups having 1–6 carbon atoms, such as methyl, ethyl, n-propyl, i-propyl, n-butyl, i-butyl, t-butyl, amyl and hexyl groups, with a methyl group being particularly preferred. Specific examples of the $1,4,4_a,8_a$-tetrahydro-$4_a\alpha$-alkenyl-$8_a\alpha$-alkyl-$1\alpha,4\alpha$-methanonaphthalene-5,8-dione derivatives (II) may include the following compounds though they are not limited to such compounds in the present invention.

(1) $1,4,4_a,9_a$-Tetrahydro-$9_a\alpha$-methyl-$4_a\alpha$-(3'-methyl-2'-butenyl)-$1\alpha,4\alpha$-methanoanthraquinone;
(2) $1,4,4_a,9_a$-Tetrahydro-$9_a\alpha$-methyl-$4_a\alpha$-(3',7'-dimethyl-2',6'-octadienyl)-$1\alpha,4\alpha$-methanoanthraquinone;
(3) $1,4,4_a,9_a$-Tetrahydro-$9_a\alpha$-methyl-$4_a\alpha$-(3',7',11'-trimethyl-2',6',10'-dodecatrienyl)-$1\alpha,4\alpha$-methanoanthraquinone;
(4) $1,4,4_a,9_a$-Tetrahydro-$9_a\alpha$-methyl-$4_a\alpha$-(3',7',11',15'-tetramethyl-2',6',10',14'-hexadecatetraenyl)-$1\alpha,4\alpha$-methanoanthraquinone;
(5) $1,4,4_a,9_a$-Tetrahydro-$9_a\alpha$-methyl-$4_a\alpha$-(3',7',11',15',19'-pentamethyl-2',6',10',14',18'-eicosadecaheptaenyl)-$1\alpha,4\alpha$-methanoanthraquinone;
(6) $1,4,4_a,9_a$-Tetrahydro-$9_a\alpha$-methyl-$4_a\alpha$-(3',7',11',15'-tetramethyl-2'-hexadecaenyl)-$1\alpha,4\alpha$-methanoanthraquinone; and
(7) $1,4,4_a,8_a$-Tetrahydro-6,7-dimethoxy-$4_a\alpha$-methyl-$8_a\alpha$-solanesyl-$1\alpha,4\alpha$-methanonaphthalene-5,8-dione.

The quinone derivatives according to the first and second aspects of the present invention are represented by the following formula (III):

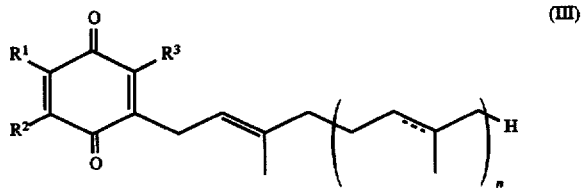
(III)

In the formula (III), $R^1$, $R^2$, $R^3$, n and a linkage $=\!=\!=$ have the same meaning as defined above. Specific examples of the quinone derivatives (III) may include the following compounds though they are not limited to such compounds in the present invention.

(1) 2-Methyl-3-(3'-methyl-2'-butenyl)-1,4-napthoquinone;

(2) 2-Methyl-3-(3',7'-dimethyl-2',6'-octadienyl)-1,4-naphthoquinone;

(3) 2-Methyl-3-(3',7',11'-trimethyl-,2', 6',10'-dodecatrienyl)-1,4-naphthoquinone;

(4) 2-Methyl-3-(3',7',11',15'-tetramethyl-2',6',10',14'-hexadecatetraenyl)-1,4-naphthoquinone; (common name: menatetrenone [vitamin $K_2$]);

(5) 2-Methyl-3-(3',7',11',15'-tetramethyl-2'-hexadecaenyl)- 1,4-naphthoquinone (common name: phytonadione [vitamin $K_1$]);

(6) 2-Methyl-3-(3',7',11',15',19'-pentamethyl-2',6',10',14', 18'-eicosadecaheptaenyl)-1,4-naphthoquinone; and (7) 2-Methyl-3-solanesyl-5,6-dimethoxy-1,4-benzoquinone.

The quinone derivatives according to the third and fourth aspects of the present invention are represented by the following formula (VI):

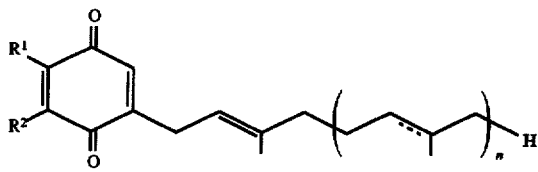

(VI)

In the formula (VI), $R^1$, $R^2$, n and a linkage $\underset{=}{\phantom{=}}$ have the same meaning as defined above. Specific examples of the quinone derivatives (VI) may include the following compounds though they are not limited to such compounds in the present invention.

(1) 2-(3'-Methyl-2'-butenyl)-1,4-naphthoquinone;

(2) 2-(3',7'-Dimethyl-2',6'-octadienyl)-1,4-naphthoquinone;

(3) 2-(3',7',11'-Trimethyl-2',6',10'-dodecatrienyl)-1,4-naphthoquinone;

(4) 2-(3',7',11',15'-Tetramethyl-2',6',10',14'-hexadecatetraenyl)-1,4-naphthoquinone;

(5) 2-(3',7',11',15',19'-Pentamethyl-2',6',10',14',18'-eicosadecaheptaenyl)-1,4-naphthoquinone; and (6) 5-Solanesyl-2,3-dimethoxy-1,4-benzoquinone.

The individual steps in the preparation processes according to the present invention will hereinafter be described in detail (see the chemical reaction formula shown on page 6).

Step 1

This step is a process in which cyclopentadiene is added to 1,4-naphthoquinone, 1,4-benzoquinone or the like in accordance with the Diels-Alder reaction to prepare a 1,4,$4_a$,$8_a$-tetrahydro-1α,4α-methanonaphthalene-5,8-dione derivative (IV). In general, this addition can be performed in accordance with the usual Diels-Alder reaction. In the present invention, however, the derivative (IV) can be prepared by adding cyclopentadiene at room temperature to 1,4-naphthoquinone, 1,4-benzoquinone or the like which may or may not be dissolved in a solvent.

In the case where the solvent is used, no limitation is imposed on the solvent to be used so long as it is inert on 1,4-naphthoquinone, 1,4-benzoquinone or the like, and cyclopentadiene. Specific examples thereof may include methanol, ethanol, n-propanol, i-propanol, n-butanol, i-butanol, t-butanol, formic acid, acetic acid, propionic acid, butyric acid, methylene chloride, chloroform, carbon tetrachloride, trichlene, nitromethane, tetrahydrofuran, 1,2-dimethoxyethane, ethyl ether, isopropyl ether, methyl acetate, ethyl acetate, propyl acetate, methyl propionate, ethyl propionate, methyl butyrate, ethyl butyrate, acetone, 2-butanone, 1,4-dioxane, 1,3-dioxolan, N,N-dimethylformamide, dimethylsulfoxide, hexamethylphosphoric triamide (HMPA), hexamethylphosphorous triamide (HMPT), benzene, toluene, xylene, pentane, n-hexane, octane, ligroin, petroleum ether, nitrobenzene, etc., with methanol, ethanol, n-propanol, i-propanol, n-butanol, i-butanol, t-butanol, formic acid, acetic acid and propionic acid being more preferred.

No limitation is imposed on the amount of the solvent to be used. However, it is generally used in an amount of about 0.5–100 parts by volume, preferably about 0.5–50 parts by volume, more preferably about 1–20 parts by volume per part by weight of 1,4-naphthoquinone or the like. Incidentally, the solvents may be used either singly or in any combination thereof.

Further, no limitation is imposed on the amount of cyclopentadiene to be used in the present invention. However, it is generally used in an amount of about 1–10 equivalents, preferably about 1–7 equivalents, more preferably about 1–5 equivalents based on 1,4-naphthoquinone or the like.

The reaction in this step may be conducted in a temperature range of from −40° C. to a reflux temperature of the solvent, generally, at room temperature. The reaction is generally completed in about 1–6 hours.

Incidentally, the 1,4,$4_a$,$8_a$-tetrahydro-1α,4α-methanonaphthalene-5,8-dione derivative (IV) formed can be purified by the conventionally-known method such as recrystallization or column chromatography on silica gel.

Step 2

This step is a process in which an allyl derivative (V) is added to the 1,4,$4_a$,$8_a$-tetrahydro-1α,4α-methanonaphthalene-5,8-dione derivative (IV) obtained in Step 1 in the presence of a base to prepare a 1,4,$4_a$,$8_a$-tetrahydro-$4_a$α-alkenyl-1α,4α-methanonaphthalene-5,8-dione derivative (I). This process may be generally carried out in accordance with the conventionally-known method for the C-alkylation of a methylene or methine group attached to an α position of a ketone. In the present invention, however, the derivative (I) can be prepared either by dissolving or suspending a base in a solvent, adding the 1,4,$4_a$,$8_a$-tetrahydro-1α,4α-methanonaphthalene-5,8-dione derivative (IV) thereto and then adding the allyl derivative (V), or by dissolving the 1,4,$4_a$,$8_a$-tetrahydro-1α,4α-methanonaphthalene-5,8-dione derivative (IV) in a solvent, adding the base thereto and then adding the allyl derivative (V). In this step, the reaction may preferably be conducted in an inert gas stream. However, no limitation is imposed on this process, and it may hence be performed in no inert gas stream.

When the allyl derivative (V) is added to the 1,4,$4_a$,$8_a$-tetrahydro-1α,4α-methanonaphthalene-5,8-dione derivative (IV), the reaction is conducted in the presence of the base. Specific examples of the base may include sodium methoxide, sodium ethoxide, potassium methoxide, potassium ethoxide, potassium t-butoxide, sodium hydride, potassium hydride, calcium hydride, n-butyllithium, sodium amide, lithium amide, lithium dimethylamide, lithium diethylamide, lithium diisopropylamide, lithium dicyclohexylamide, sodium hydroxide, potassium hydroxide, sodium carbonate, potassium carbonate, etc.

No limitation is imposed on the amount of the base to be used. However, it is generally used in an amount of about 0.8–10 equivalents, preferably about 0.9–7 equivalents, more preferably about 1.0–5 equivalents based on the 1,4,$4_a$,$8_a$-tetrahydro-1α,4α-methanonaphthalene-5,8-dione derivative (IV).

No limitation is also imposed on the amount of the allyl derivative (V) to be used. However, it is generally used in an amount of 0.8–10 equivalents, preferably about 0.9–5 equivalents, more preferably about 1.0–3 equivalents based on the 1,4,4$_a$,8$_a$-tetrahydro-1α,4α-methanonaphthalene-5,8-dione derivative (IV).

Further, no limitation is imposed on the solvents to be used in this step so long as they are inert on the base, 1,4,4$_a$,8$_a$-tetrahydro-1α,4α-methanonaphthalene-5,8-dione derivative (IV) or allyl derivative (V). Specific examples thereof may include tetrahydrofuran, 1,2-dimethoxyethane, 2-methoxyethyl ether, ethyl ether, isopropyl ether, methyl acetate, ethyl acetate, propyl acetate, methyl propionate, ethyl propionate, methyl butyrate, ethyl butyrate, N,N-dimethylformamide, dimethylsulfoxide, 1,4-dioxane, 1,3-dioxolan, hexamethylphosphoric triamide (HMPA), hexamethylphosphorous triamide (HMPT), benzene, toluene, xylene, n-hexane, pentane, octane, ligroin, petroleum ether, etc. Of these, tetrahydrofuran, 1,2-dimethoxyethane, 2-methoxyethyl ether, ethyl ether, N,N-dimethylformamide, dimethylsulfoxide, hexamethylphosphoric triamide, hexamethylphosphorous triamide, toluene, n-hexane and octane are preferred, with tetrahydrofuran, 1,2-dimethoxyethane, 2-methoxyethyl ether and n-hexane being more preferred.

No limitation is imposed on the amount of the solvent to be used. However, it is generally used in an amount of about 0.5–100 parts by volume, preferably about 0.5–50 parts by volume, more preferably about 1–20 parts by volume per part by weight of the 1,4,4$_a$,8$_a$-tetrahydro-1α,4α-methanonaphthalene-5,8-dione derivative (IV). Incidentally, the solvents may be used either singly or in any combination thereof.

The reaction in this step may be conducted in a temperature range of from −80° C. to a reflux temperature of the solvent, preferably from −40° C. to 20° C., more preferably from −20° C. to 10° C. With respect to the reaction time in this step, the reaction of the base and 1,4,4$_a$,8$_a$-tetrahydro-1α,4α-methanonaphthalene-5,8-dione derivative (IV) is generally conducted for 10 minutes to 2 hours, and the whole reaction is completed in about 10 minutes to 2 hours after the subsequent addition of the allyl derivative (V).

Incidentally, the 1,4,4$_a$,8$_a$-tetrahydro-4$_a$α-alkenyl-1α,4α-methanonaphthalene-5,8-dione derivative (I) formed can be purified by the conventionally-known method such as recrystallization, column chromatography on silica gel or molecular distillation.

Step 3

This step is a process for preparing a 1,4,4$_a$,8$_a$-tetrahydro-4$_a$α-alkenyl-8$_a$α-alkyl-1α,4α-methanonaphthalene-5,8-dione derivative (II) in which R$^3$ is not a hydrogen atom, but an alkyl group. The derivative (II) can be prepared by reacting the 1,4,4$_a$,8$_a$-tetrahydro-4$_a$α-alkenyl-1α,4α-methanonaphthalene-5,8-dione derivative (I) obtained in Step 2 with an alkyl halide (R$^3$X) in the presence of a base. The term "alkyl halide" as used in the present invention means a compound in which a lower alkyl group R$^3$ having 1–6 carbon atoms is bonded to a halogen atom X. The halogen atom X means an iodine, bromine, chlorine or fluorine atom. Specific examples of the alkyl halide may include methyl iodide, ethyl iodide, n-propyl iodide, i-propyl iodide, n-butyl iodide, i-butyl iodide, methyl bromide, ethyl bromide, n-propyl bromide, i-propyl bromide, n-butyl bromide, i-butyl bromide, etc. Of these, methyl iodide and methyl bromide are more preferred.

As specific examples of the base used in this step, may also be mentioned the same bases as those used in the addition of the allyl derivative (V) to the 1,4,4$_a$,8$_a$-tetrahydro-1α,4α-methanonaphthalene-5,8-dione derivative (IV) in Step 2. However, potassium t-butoxide, sodium hydride, potassium hydride, calcium hydride, n-butyllithium, sodium amide, lithium amide, lithium dimethylamide, lithium diethylamide, lithium diisopropylamide and lithium dicyclohexylamide are preferred.

No limitation is imposed on the amount of the base to be used. However, it is generally used in an amount of about 0.8–10 equivalents, preferably about 0.9–7 equivalents, more preferably about 1.0–5 equivalents based on the 1,4,4$_a$,8$_a$-tetrahydro-4$_a$α-alkenyl-1α,4α-methanonaphthalene-5,8-dione derivative (I).

Further, no limitation is imposed on the solvents to be used in this step so long as they are inert on the base, alkyl halide or 1,4,4$_a$,8$_a$-tetrahydro-4$_a$α-alkenyl-1α,4α-methanonaphthalene-5,8-dione derivative (I). Specific examples thereof may include tetrahydrofuran, 1,2-dimethoxyethane, 2-methoxyethyl ether, ethyl ether, isopropyl ether, methyl acetate, ethyl acetate, propyl acetate, methyl propionate, ethyl propionate, methyl butyrate, ethyl butyrate, N,N-dimethylformamide, dimethylsulfoxide, 1,4-dioxane, 1,3-dioxolan, hexamethylphosphoric triamide, hexamethylphosphorous triamide, benzene, toluene, xylene, n-hexane, pentane, octane, ligroin, petroleum ether, etc. Of these, tetrahydrofuran, 1,2-dimethoxyethane, 2-methoxyethyl ether, ethyl ether, N,N-dimethylformamide, dimethylsulfoxide, hexamethylphosphoric triamide, hexamethylphosphorous triamide, toluene, n-hexane and octane are preferred, with tetrahydrofuran, 1,2-dimethoxyethane, 2-methoxyethyl ether and n-hexane being more preferred.

No limitation is imposed on the amount of the solvent to be used. However, it is generally used in an amount of about 0.5–100 parts by volume, preferably about 0.5–50 parts by volume, more preferably about 1–20 parts by volume per part by weight of the 1,4,4$_a$,8$_a$-tetrahydro-4$_a$α-alkenyl-1α,4α-methanonaphthalene-5,8-dione derivative (I). Incidentally, the solvents may be used either singly or in any combination thereof.

The reaction in this step may be conducted in a temperature range of from −80° C. to a reflux temperature of the solvent, preferably from −40° C. to 20° C., more preferably from −20° C. to 10° C. With respect to the reaction time in this step, the reaction of the base and 1,4,4$_a$,8$_a$-tetrahydro-4$_a$α-alkenyl-1α,4α-methanonaphthalene-5,8-dione derivative (I) is generally conducted for 10 minutes to 2 hours, and the whole reaction is completed in about 10 minutes to 2 hours after the subsequent addition of the alkyl halide.

The 1,4,4$_a$,8$_a$-tetrahydro-4$_a$α-alkenyl-8$_a$α-alkyl-1α,4α-methanonaphthalene-5,8-dione derivative (II) formed can be purified by the conventionally-known method such as recrystallization or column chromatography on silica gel.

Step 4

This step is a process in which the 1,4,4$_a$,8$_a$-tetrahydro-4$_a$α-alkenyl-8$_a$α-alkyl-1α,4α-methanonaphthalene-5,8-dione derivative (II) obtained in Step 3 is heated to conduct a Retro Diels-Alder reaction, thereby preparing a quinone derivative (III). This step can be conducted in accordance with the general procedure for the Retro Diels-Alder reaction.

More specifically, the 1,4,4$_a$,8$_a$-tetrahydro-4$_a$α-alkenyl-8$_a$α-alkyl-1α,4α-methanonaphthalene-5,8-dione derivative (II) can be heated in an inert gas stream to prepare the quinone derivative (III). In this reaction, it is preferable to use a solvent. However, no solvent may be used if the 1,4,4$_a$,8$_a$-tetrahydro-4$_a$α-alkenyl-8$_a$α-alkyl-1α,4α-methanonaphthalene-5,8-dione derivative (II) is liquid or oily.

No limitation is imposed on the solvent to be used so long as it is inert on the $1,4,4_a,8_a$-tetrahydro-$4_a\alpha$-alkenyl-$8_a\alpha$-alkyl-$1\alpha,4\alpha$-methanonaphthalene-5,8-dione derivative (II). Specific examples thereof may include n-butanol, i-butanol, pentyl alcohol, ethylene glycol, propylene glycol, propyl butyrate, butyl butyrate, butyl ether, pentyl ether, cyclohexanone, 2-heptanone, 3-heptanone, 4-heptanone, N,N-dimethylformamide, dimethylsulfoxide, 1,4-dioxane, 1,3-dioxolan, octane, decane, benzene, toluene, xylene, benzyl alcohol, nitrobenzene, etc., with toluene, xylene, ethylene glycol, propylene glycol, propyl butyrate and butyl butyrate being more preferred.

No limitation is imposed on the amount of the solvent to be used. However, it is generally used in an amount of about 0.5–100 parts by volume, preferably about 0.5–50 parts by volume, more preferably about 1–20 parts by volume per part by weight of the $1,4,4_a,8_a$-tetrahydro-$4_a\alpha$-alkenyl-$8_a\alpha$-alkyl-$1\alpha,4\alpha$-methanonaphthalene-5,8-dione derivative (II). Incidentally, the solvents may be used either singly or in any combination thereof.

The reaction in this step may be conducted in a temperature range of from 60° C. to a reflux temperature of the solvent, preferably from 80° C. to the reflux temperature of the solvent, more preferably from 100° C. to the reflux temperature of the solvent. The reaction is generally completed in about 10 minutes to 2 hours.

The quinone derivative (III) formed can be purified by the conventionally-known method such as recrystallization, column chromatography on silica gel, HPLC or molecular distillation.

Step 5

This step is a process in which the $1,4,4_a,8_a$-tetrahydro-$4_a\alpha$-alkenyl-$1\alpha,4\alpha$-methanonaphthalene-5,8-dione derivative (I) obtained in Step 2 is heated to conduct a Retro Diels-Alder reaction, thereby preparing a quinone derivative (VI). In this step, reaction and purification may be conducted in the same manner as in Step 4.

The $4_a,5,8,8_a$-tetrahydro-$4_a\alpha$-alkenyl-$5\alpha,8\alpha$-1,4-benzoquinone derivatives represented by the following formula (I):

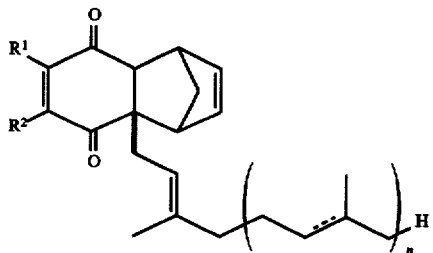

wherein $R^1$, $R^2$, n and a linkage --- have the same meaning as defined above, are new substances and useful as intermediates for the preparation of the quinone derivatives (III) serving as drugs such as vitamin K derivatives, which play an important role in the vital body as hematostatic vitamins, and coenzyme Q derivatives, which are useful as therapeutic agents for ischemic heart diseases such as congestive heart failure. Specific examples of the $4_a,5,8,8_a$-tetrahydro-$4_a\alpha$-alkenyl-$5\alpha,8\alpha$-1,4-benzoquinone derivatives (I) may include the following compounds though they are not limited to such compounds in the present invention.

(1) $1,4,4_a,9_a$-Tetrahydro-$4_a\alpha$-(3'-methyl-2'-butenyl)-$1\alpha,4\alpha$-methanoanthraquinone;

(2) $1,4,4_a,9_a$-Tetrahydro-$4_a\alpha$-(3',7'-dimethyl-2',6'-octadienyl)-$1\alpha,4\alpha$-methanoanthraquinone;

(3) $1,4,4_a,9_a$-Tetrahydro-$4_a\alpha$-(3',7',11'-trimethyl-2',6',10'-dodecatrienyl)-$1\alpha,4\alpha$-methanoanthraquinone;

(4) $1,4,4_a,9_a$-Tetrahydro-$4_a\alpha$-(3',7',11',15'-tetramethyl-2',6',10',14'-hexadecatetraenyl)-$1\alpha,4\alpha$-methanoanthraquinone;

(5) $1,4,4_a,9_a$-Tetrahydro-$4_a\alpha$-(3',7',11',15',19'-pentamethyl-2',6',10',14',18'-eicosadecaheptaenyl)-$1\alpha,4\alpha$-methanoanthraquinone;

(6) $1,4,4_a,9_a$-Tetrahydro-$4_a\alpha$-(3',7',11',15'-tetramethyl-2'-hexadecaenyl)-$1\alpha,4\alpha$-methanoanthraquinone; and (7) $1,4,4_a,8_a$-Tetrahydro-6,7-dimethoxy-$4_a\alpha$-solanesyl-$1\alpha,4\alpha$-methanonaphthalene-5,8-dione.

Preparation Example for providing a starting material required to carry out the present invention will hereinafter be described prior to Examples.

PREPARATION EXAMPLE 1

Synthesis of $1,4,4_a,9_a$-tetrahydro-$1\alpha,4\alpha$-methanoanthraquinone

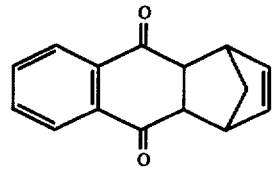

In a mixture of methanol (200 ml) and acetic acid (200 ml), were dissolved 87 g (550 mmol) of 1,4-naphthoquinone, to which 72 g (1100 mmol) of cyclopentadiene were added dropwise over 1 hour. Thereafter, the resultant mixture was stirred for 2 hours. The liquid reaction mixture was distilled under reduced pressure, and the residue was subjected to recrystallization from methanol, thereby obtaining 115.6 g of the title compound (yield: 94%).

Melting point: 105°–107° C. (decomposed) [value in literature: 116°–117° C., Liebigs Annalen der Chemie, 348, 31 (1906)]

The present invention will hereinafter be described specifically by the following Examples. It should be borne in mind that the present invention is not limited to and by these examples only.

EXAMPLE 1

Synthesis of $1,4,4_a,9_a$-tetrahydro-$4_a\alpha$-(3'-methyl-2'-butenyl)-$1\alpha,4\alpha$-methanoanthraquinone

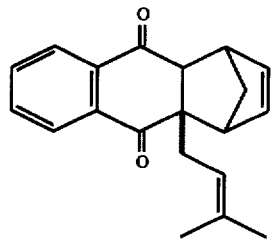

In tetrahydrofuran (50 ml), were dissolved 19 g (100 mmol) of a 28% solution of sodium methoxide in methanol, to which a solution of 11.2 g (50 mmol) of $1,4,4_a,9_a$-tetrahydro-$1\alpha,4\alpha$-methanoanthraquinone in tetrahydrofuran (100 ml) was added dropwise over 30 minutes at 0°–5° C. in an argon stream. The resultant mixture was stirred for 30 minutes as it is. A solution of 12.0 g (50 mmol) of 3'-methyl- 2'-butenyl bromide in tetrahydrofuran (50 ml) was then added dropwise to the liquid reaction mixture over 30 minutes with the liquid reaction mixture kept at 0°–5° C., followed by its stirring further for 1 hour. The resultant liquid reaction mixture was added into 0.1N hydrochloric acid (200 ml) to make extraction twice with toluene (200 ml ×2). After drying an organic layer, it was concentrated under reduced pressure to obtain a residue in the form of a brown oil. This residue was purified by column chromatography on silica gel (n-hexane:toluene system), thereby obtaining 13.1 g of the title compound as pale yellow crystals (yield: 90%, HPLC purity: 98.9%).

Melting point: 97°–99° C.

IR (cm$^{-1}$): 1680, 1650 (C=O).

$^1$H-NMR (90 MHz, CDCl$_3$), δ(ppm): 1.4(2H,dd,J=3 Hz), 1.42(3H,s), 1.5(3H,s), 2.4(1H,br-d), 2.7(1H,br-d), 2.8(1H, br-d), 3.3(2H,br-d), 4.8(1H,t,J=6 Hz), 6.3(1H,dd,J=10 Hz), 6.5(1H,dd,J=10Hz), 7.7(2H,dd,J=6 Hz), 8.1(2H,dd,J=6 Hz)

FAB-MS: m/z=292 (M$^+$).

EXAMPLE 2

Synthesis of 2-(3'-methyl-2'-butenyl)-1,4,-naphthoquinone

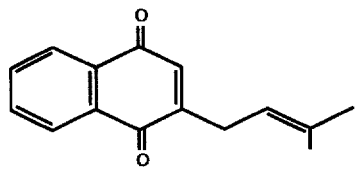

In toluene (20 ml), were dissolved 2.9 g (10 mmol) of 1,4,4$_a$,9$_a$-tetrahydro-4$_a$α-(3'-methyl-2'-butenyl)-1α,4α-methanoanthraquinone, and the resultant solution was refluxed for 30 minutes in an argon stream. The liquid reaction mixture was concentrated under reduced pressure to obtain a residue in the form of a yellowish-orange oil. This residue was purified by column chromatography on silica gel (n-hexane:toluene system), thereby obtaining 2.2 g of the title compound as a yellow oil (yield: 98%).

This product consisted with a standard sample in TLC, HPLC and capillary GC.

EXAMPLE 3

Synthesis of 1,4,4$_a$,9$_a$-tetrahydro-9$_a$α-methyl-4$_a$α-(3'-methyl -2'-butenyl)-1α,4α-methanoanthraquinone

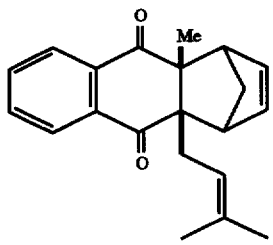

In tetrahydrofuran (50 ml), were dissolved 7.9 g (70 mmol) of potassium t-butoxide, to which a solution of 10.4 g (36 mmol) of 1,4,4$_a$,9$_a$-tetrahydro-4$_a$α-(3'-methyl-2'-butenyl)-1α,4α-methanoanthraquinone in tetrahydrofuran (50 ml) was added dropwise over 30 minutes at 0°–5° C. in an argon stream. The resultant mixture was stirred for 30 minutes as it is. A solution of 5.5 g (39 mmol) of methyl iodide in tetrahydrofuran (30 ml) was then added dropwise to the liquid reaction mixture over 30 minutes with the liquid reaction mixture kept at 0°–5° C., followed by its stirring further for 1 hour. The resultant liquid reaction mixture was added into 0.1N hydrochloric acid (100 ml) to make extraction twice with toluene (100 ml×2). After drying an organic layer, it was concentrated under reduced pressure to obtain a residue in the form of a yellowish-orange oil. This residue was purified by column chromatography on silica gel (n-hexane:toluene system), thereby obtaining 9.6 g of the title compound as yellow crystals (yield: 87%, HPLC purity: 99.2%).

Melting point: 94°–96° C.

IR (cm$^{-1}$): 1675, 1645 (C=O).

$^1$H-NMR (90 MHz, CDCl$_3$), δ(ppm): 1.3(3H,s), 1.4(2H, dd,J=3 Hz), 1.5(3H,s), 1.54(3H,s), 2.4(1H,br-d), 3.45(2H, br-d), 4.82(1H,t,J=6 Hz), 6.4(2H,dd,J=10 Hz), 7.65(2H,dd, J=6 Hz), 8.0 (2H,dd,J=6 Hz).

FAB-MS: m/z=306 (M$^+$).

EXAMPLE 4

Synthesis of 2-methyl-(3'-methyl-2'-butenyl)-1,4-naphthoquinone

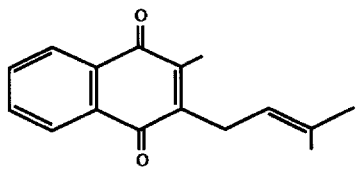

In toluene (30 ml), were dissolved 3.1 g (10 mmol) of 1,4,4$_a$,9$_a$-tetrahydro-9$_a$α-methyl-4$_a$α-(3'-methyl-2'-butenyl)-1α,4α-methanoanthraquinone, thereby conducting a Retro Diels-Alder reaction and post-treatment in the same manner as in Example 2 to obtain 2.4 g of the title compound as a yellow oil (yield: 99%).

This product consisted with a standard sample in TLC, HPLC and capillary GC.

EXAMPLE 5

Synthesis of 1,4,4$_a$,9$_a$-tetrahydro-4$_a$α-[(2'E)-3',7'-dimethyl-2'E-2',6'-octadienyl]-1α,4α-methanoanthraquinone

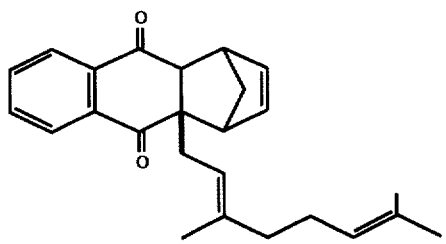

In tetrahydrofuran (80 ml), were dissolved 7.6 g (40 mmol) of a 28% solution of sodium methoxide in methanol, and 4.4 g (20 mmol) of 1,4,4$_a$,9$_a$-tetrahydro-1α,4α-methanoanthraquinone and 4.4 g (20 mmol) of (2E)-geranyl bromide were used to conduct reaction in the same manner as in Example 1, thereby obtaining 6.5 g of the title compound as a yellow oil (yield: 90%, HPLC purity: 99.0%).

IR (cm$^{-1}$): 1675, 1645 (C=O).

$^1$H-NMR (90 MHz, CDCl$_3$), δ(ppm): 1.42(2H,d,J=2 Hz), 1.48(6H,s), 1.5(3H,s), 1.8(2H,br), 2.2(2H,br), 2.4(1H,br-d), 2.7(1H,br-d), 2.8(1H,br-d), 3.3(2H,br-d), 4.8(1H,t,J=6 Hz), 5.0(1H,t,J=5 Hz), 6.3(1H,dd,J=10 Hz), 6.5(1H,dd,J=10 Hz), 7.7(2H,dd,J=6 Hz), 8.1(2H,dd,J=6 Hz).

FAB-MS: m/z=360 (M$^+$).

EXAMPLE 6

Synthesis of 2-[(2'E)-3',7'-dimethyl-2',6'-octadienyl]-1,4-naphthoquinone

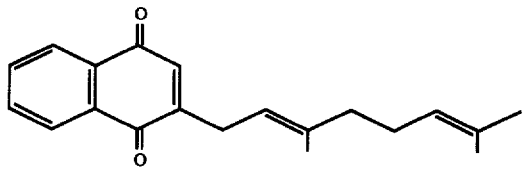

A solution of 1.8 g (5 mmol) of 1,4,4$_a$,9$_a$-tetrahydro-4$_a$α-[(2'E)-3',7'-dimethyl-2',6'-octadienyl]-1α,4α-methanoanthraquinone in toluene (20 ml) was used to conduct a Retro Diels-Alder reaction and post-treatment in the same manner as in Example 2, thereby obtaining 1.5 g of the title compound as a yellow oil (yield: 99%, HPLC purity: 99.3%).

This product consisted with a standard sample in TLC, HPLC and capillary GC.

EXAMPLE 7

Synthesis of 1,4,4$_a$,9$_a$-tetrahydro-9$_a$α-methyl-4$_a$α-[(2'E)-3',7'-dimethyl-2',6'-octadienyl]-1α,4α-methanoanthraquinone

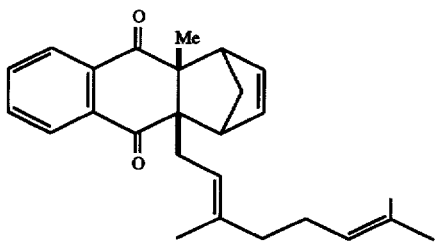

In tetrahydrofuran (50 ml), were dissolved 1.1 g (10 mmol) of potassium t-butoxide, and 1.8 g (5 mmol) of 1,4,4$_a$,9$_a$-tetrahydro-4$_a$α-[(2'E)-3',7'-dimethyl-2',6'-octadienyl]-1α,4α-methanoanthraquinone and 0.85 g (6 mmol) of methyl iodide were used to conduct reaction in the same manner as in Example 3, thereby obtaining 1.7 g of the title compound as yellow crystals (yield: 89%, HPLC purity: 99.4%).

Melting point: 65°–67° C.

IR (cm$^{-1}$): 1675, 1645 (C=O).

$^1$H-NMR (90 MHz, CDCl$_3$), δ(ppm): 1.3(3H,s), 1.42(2H, dd,J=2 Hz), 1.45(3H,s), 1.5(3H,s), 1.8(3H,s), 2.1–2.3(4H, br), 2.4(2H,br-dd), 3.4(2H,br-d), 4.8(1H,t,J=5 Hz), 4.9(1H, t,J=5 Hz), 6.4 (2H,dd,J=10 Hz), 7.65(2H,dd,J=6 Hz), 8.0 (2H,dd,J=6 Hz).

FAB-MS: m/z=374 (M$^+$).

EXAMPLE 8

Synthesis of 2-methyl-3-[(2'E)-3',7'-dimethyl-2',6'-octadienyl]-1,4-naphthoquinone

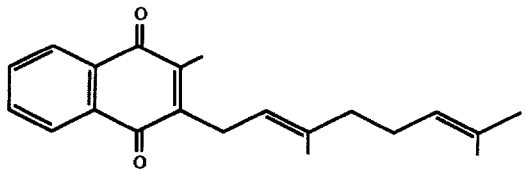

In toluene (20 ml), were dissolved 1.7 g (4.4 mmol) of 1,4,4$_a$,9$_a$-tetrahydro-9$_a$α-methyl-4$_a$α-[(2'E)-3',7'-dimethyl-2',6'-octadienyl]-1α,4α-methanoanthraquinone, thereby conducting a Retro Diels-Alder reaction and post-treatment in the same manner as in Example 2 to obtain 1.5 g of the title compound as a yellow oil (yield: 99%, HPLC purity: 99.4%).

This product consisted with a standard sample in TLC, HPLC and capillary GC.

EXAMPLE 9

Synthesis of 1,4,4$_a$,9$_a$-tetrahydro-4$_a$α-[(2'E,6'E)-3', 7',11'-trimethyl-2',6',10'-dodecatrienyl]-1α,4α-methanoanthraquinone

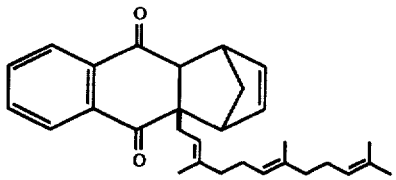

In tetrahydrofuran (150 ml), were dissolved 15.0 g (80 mmol) of a 28% solution of sodium methoxide in methanol, and 8.8 g (40 mmol) of 1,4,4$_a$,9$_a$-tetrahydro-1α,4α-methanoanthraquinone and 11.6 g (40 mmol) of (2E,6E)-farnesyl bromide were used to conduct reaction in the same manner as in Example 1, thereby obtaining 15.4 g of the title compound as a yellow oil (yield: 90%, HPLC purity: 98.9%).

IR (cm$^{-1}$): 1675, 1645 (C=O).

$^1$H-NMR (90 MHz, CDCl$_3$), δ(ppm): 1.4(2H,dd,J=2 Hz), 1.6(6H,s), 1.75(3H,s), 1.8(3H,s), 2.0–2.2(8H,br), 2.35(1H, br-d), 2.7(1H,br-d), 2.8(1H,br-d), 3.37(2H,br-d), 4.9(3H,t, J=6 Hz), 6.4(1H,dd,J=10 Hz), 6.6(1H,dd,J=10 Hz), 7.65(2H, dd,J=6 Hz), 8.03(2H,dd,J=6 Hz).

FAB-MS: m/z=428 (M$^+$).

EXAMPLE 10

Synthesis of 2-[(2'E,6'E)-3',7',11'-trimethyl-2',6',10'-dodecatrienyl]-1,4-naphthoquinone

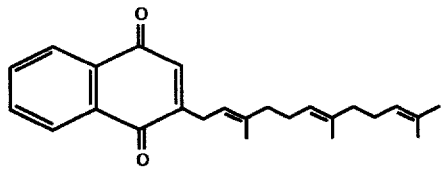

A solution of 4.3 g (10 mmol) of 1,4,4$_a$,9$_a$-tetrahydro-4$_a$α-[(2'E,6'E)-3',7',11'-trimethyl-2',6',10'-dodecatrienyl]-1α,4α-methanoanthraquinone in toluene (20 ml) was used to conduct a Retro Diels-Alder reaction and post-treatment in the same manner as in Example 2, thereby obtaining 3.6 g of the title compound as a yellow oil (yield: 99%, HPLC purity: 99.2%).

This product consisted with a standard sample in TLC, HPLC and capillary GC.

EXAMPLE 11

Synthesis of 1,4,4$_a$,9$_a$-tetrahydro-9$_a$α-methyl-4$_a$α-[(2'E,6'E)-3',7',11'-trimethyl-2',6',10'-dodecatrienyl]-1α,4α-methanoanthraquinone

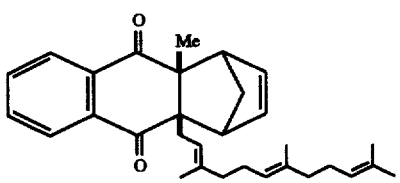

In tetrahydrofuran (80 ml), were dissolved 2.2 g (20 mmol) of potassium t-butoxide, and 4.3 g (10 mmol) of 1,4,4$_a$,9$_a$-tetrahydro-9$_a$α-methyl-4$_a$α-[(2'E, 6'E)-3',7',11'-trimethyl-2',6',10'-dodecatrienyl]-1α,4α-methanoanthraquinone and 1.55 g (11 mmol) of methyl iodide were used to conduct reaction in the same manner as in Example 3, thereby obtaining 4.1 g of the title compound as a yellow oil (yield: 93%, HPLC purity: 99.5%).

IR (cm$^{-1}$): 1675, 1645 (C=O).

$^1$H-NMR (90 MHz, CDCl$_3$), δ(ppm): 1.33(3H, s), 1.4(2H, dd,J=2 Hz), 1.6(6H,s), 1.73(3H,s), 1.8(3H,s), 2.0–2.1(8H, br), 2.4(2H,br-d), 3.35(2H,br-d), 4.85(3H,t,J=6 Hz), 6.5(2H, dd,J=10 Hz), 7.67(2H,dd,J=5 Hz), 8.03(2H,dd,J=5 Hz).

FAB-MS: m/z=442 (M$^+$).

EXAMPLE 12

Synthesis of 2-methyl-3-[(2'E,6'E)-3',7',11'-trimethyl-2',6',10'-dodecatrienyl]-1,4-naphthoquinone

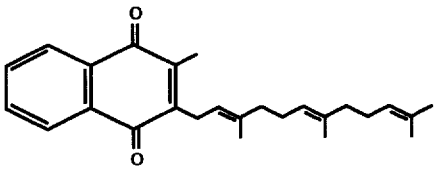

In toluene (20 ml), were dissolved 4.0 g (9 mmol) of 1,4,4$_a$,9$_a$-tetrahydro-9$_a$α-methyl-4$_a$α-[(2'E,6'E)-3',7',11'-trimethyl-2',6',10'-dodecatrienyl]-1α,4α-methanoanthraquinone, thereby conducting a Retro Diels-Alder reaction and post-treatment in the same manner as in Example 2 to obtain 3.7 g of the title compound as a yellow oil (yield: 97.3%, HPLC purity: 98.9%).

This product consisted with a standard sample in TLC, HPLC and capillary GC.

EXAMPLE 13

Synthesis of 1,4,4$_a$,9$_a$-tetrahydro-4$_a$α-[(2'E,6'E, 10'E)-3',7',11',15'-tetramethyl-2',6',10',14'-hexadecatetraenyl]-1α,4α-methanoanthraquinone

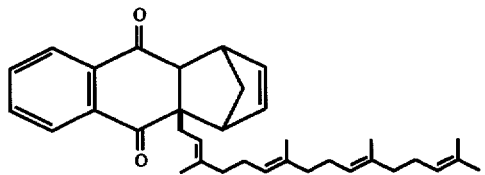

In tetrahydrofuran (150 ml), were dissolved 19.0 g (100 mmol) of a 28% solution of sodium methoxide in methanol, and 11.2 g (50 mmol) of 1,4,4$_a$,9$_a$-tetrahydro-1α,4α-methanoanthraquinone and 20.7 g (50 mmol) of (2E,6E, 10E)-geranylgeranyl bromide were used to conduct reaction in the same manner as in Example 1, thereby obtaining 21.7 g of the title compound as a yellow oil (yield: 88%, HPLC purity: 99.0%).

IR (cm$^{-1}$): 1675, 1645 (C=O).

$^1$H-NMR (90 MHz, CDCl$_3$), δ(ppm): 1.4(2H,dd,J=3 Hz), 1.6(9H,s), 1.72(3H,s), 1.8(3H,s), 2.0–2.1(12H,br), 2.4(1H, br-d), 2.7(1H,br-d), 2.8(1H,br-d), 3.35(2H,br-d), 4.82(3H,t, J=6 Hz), 4.9(1H,t,J=5 Hz), 6.62(2H,dd,J=10 Hz), 7.66(2H, dd,J=6 Hz), 8.02 (2H,dd,J=6 Hz).

FAB-MS: m/z=496 (M$^+$).

EXAMPLE 14

Synthesis of 2-[(2'E,6'E,10'E)-3',7',11',15'-tetramethyl-2',6',10',14'-hexadecatetraenyl]-1,4-naphthoquinone

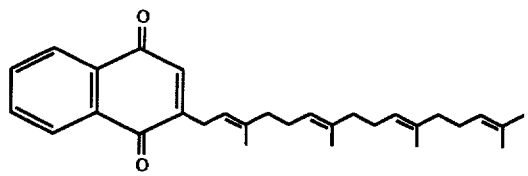

A solution of 5.0 g (10 mmol) of 1,4,4$_a$,9$_a$-tetrahydro-4$_a$α-[(2'E,6'E,10'E)-3',7',11',15'-tetramethyl-2',6',10',14'-hexadecatetraenyl]-1α,4α-methanoanthraquinone in toluene (25 ml) was used to conduct a Retro Diels-Alder reaction and post-treatment in the same manner as in Example 2, thereby obtaining 4.3 g of the title compound as a yellow oil (yield: 99%).

This product consisted with a standard sample in TLC, HPLC and capillary GC.

EXAMPLE 15

Synthesis of 1,4,4$_a$,9$_a$-tetrahydro-9$_a$α-methyl-4$_a$α-[(2'E,6'E,10'E)-3',7',11',15'-tetramethyl-2',6',10',14'-hexadecatetraenyl]-1α,4α-methanoanthraquinone

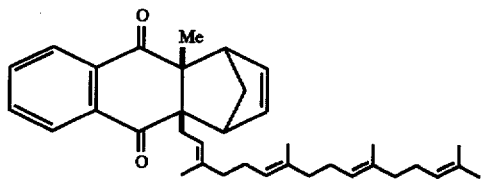

In tetrahydrofuran (80 ml), were dissolved 2.2 g (20 mmol) of potassium t-butoxide, and 5.0 g (10 mmol) of 1,4,4$_a$,9$_a$-tetrahydro-4$_a$α-[(2'E,6'E,10'E)-3',7',11',15'-tetramethyl-2',6',10',14'-hexadecatetraenyl]-1α,4α-methanoanthraquinone and 1.55 g (11 mmol) of methyl iodide were used to conduct reaction in the same manner as in Example 3, thereby obtaining 4.7 g of the title compound as a yellow oil (yield: 92%, HPLC purity: 99.2%).

IR (cm$^{-1}$): 1675, 1645 (C=O).

$^1$H-NMR (90 MHz, CDCl$_3$), δ(ppm): 1.35(3H,s), 1.4(2H, dd,J=2 Hz), 1.61(9H,s), 1.72(3H,s), 1.8(3H,s), 2.0–2.1(12H, br), 2.7(2H,br-d), 3.3(2H,br-d), 4.85(4H,t,J=6 Hz), 6.6(2H, dd,J=10 Hz), 7.6(2H,dd,J=6 Hz), 8.0(2H,dd,J=6 Hz).

FAB-MS: m/z=510 (M$^+$).

EXAMPLE 16

Synthesis of 2-methyl-3-[(2'E,6'E,10'E)-3',7',11',15'-tetramethyl-2',6',10',14'-hexadecatetraenyl]-1,4-naphthoquinone

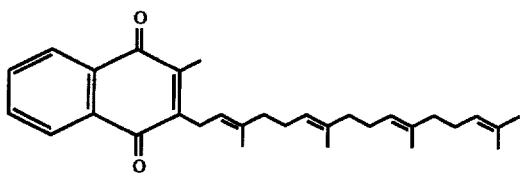

In toluene (25 ml), were dissolved 4.5 g (8.8 mmol) of 1,4,4$_a$,9$_a$-tetrahydro-9$_a$α-methyl-4$_a$α-[(2'E,6'E,10'E)-3',7',11',15'-tetramethyl-2',6',10',14'-hexadecatetraenyl]-1α,4α-methanoanthraquinone, thereby conducting a Retro Diels-Alder reaction and post-treatment in the same manner as in Example 2 to obtain 3.9 g of the title compound as a yellow oil (yield: 99%, HPLC purity: 99.6%).

This product consisted with a standard sample in TLC, HPLC and capillary GC.

EXAMPLE 17

Synthesis of 1,4,4$_a$,9$_a$-tetrahydro-4$_a$α-[(2E')-3',7',11',15'-tetramethyl-2'-hexadecaenyl]-1α,4α-methanoanthraquinone

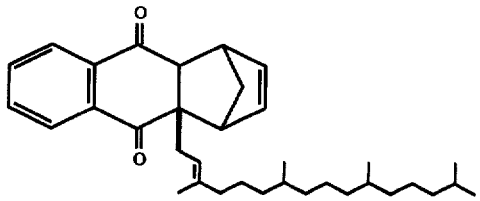

In tetrahydrofuran (100 ml), were dissolved 15.0 g (80 mmol) of a 28% solution of sodium methoxide in methanol, and 8.8 g (40 mmol) of 1,4,4$_a$,9$_a$-tetrahydro-1α,4α-methanoanthraquinone and 18.0 g (40 mmol) of (2E)-phytyl bromide were used to conduct reaction in the same manner as in Example 1, thereby obtaining 17.4 g of the title compound as a yellow oil (yield: 87%, HPLC purity: 99.7%).

IR (cm$^{-1}$): 1675, 1645 (C=O).

$^1$H-NMR (90 MHz, CDCl$_3$), δ(ppm): 0.8–0.92(12H,br-d), 1.0–1.4(18H,m), 1.78(3H,s), 1.92(2H,br), 2.4(1H,br-d), 2.7 (1H,br-d), 2.8(1H,br-d), 3.35(2H,br-d), 4.95(1H,t,J=6 Hz), 6.45(2H,$^{dd,J=}$10 Hz), 7.65(2H,dd,J=5 Hz), 8.02 (2H,dd,J=5 Hz).

FAB-MS: m/z=502 (M$^+$).

EXAMPLE 18

Synthesis of 2-[(2E')-3',7',11',15'-tetramethyl-2'-hexadecaenyl]-1,4-naphthoquinone

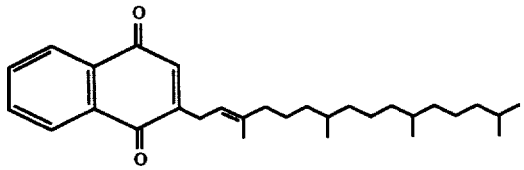

A solution of 5.0 g (10 mmol) of 1,4,4$_a$,9$_a$-tetrahydro-4$_a$α-[(2E')-3',7',11',15'-tetramethyl-2'-hexadecaenyl]-1α,4α-methanoanthraquinone in toluene (25 ml) was used to conduct a Retro Diels-Alder reaction and post-treatment in the same manner as in Example 2, thereby obtaining 4.3 g of the title compound as a yellow oil (yield: 99%, HPLC purity: 99.7%).

This product consisted with a standard sample in TLC, HPLC and capillary GC.

EXAMPLE 19

Synthesis of 1,4,4$_a$,9$_a$-tetrahydro-9$_a$α-methyl-4$_a$α-[(2E')-3',7',11',15'-tetramethyl-2'-hexadecaenyl]-1α,4α-methanoanthraquinone

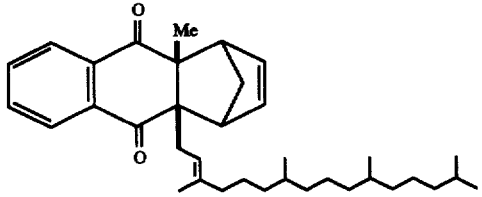

In tetrahydrofuran (80 ml), were dissolved 2.2 g (20 mmol) of potassium t-butoxide, and 5.0 g (10 mmol) of 1,4,4$_a$,9$_a$-tetrahydro-9$_a$α-methyl-4$_a$α-[(2E')-3',7',11',15'-tetramethyl-2'-hexadecaenyl]-1α,4α-methanoanthraquinone and 1.55 g (11 mmol) of methyl iodide were used to conduct reaction in the same manner as in Example 3, thereby obtaining 4.8 g of the title compound as a yellow oil (yield: 92%, HPLC purity: 99.6%).

IR (cm$^{-1}$): 1675, 1645 (C=O).

$^1$H-NMR (90 MHz, CDCl$_3$), δ(ppm): 0.8–0.9 (12H,br-d), 1.0–1.4(24H,m), 1.76(3H,s), 1.9(2H,br), 2.4(2H,br-d), 3.35 (2H,br-d), 5 4.9(1H,t,J=6 Hz), 6.4(2H,dd,J=10 Hz), 7.6(2H, dd,J=5 Hz), 8.0 (2H,dd,J=5 Hz).

FAB-MS: m/z=516 (M$^+$).

EXAMPLE 20

Synthesis of 2-methyl-3-[(2E')-3',7',11',15'-tetramethyl-2'-hexadecaenyl]-1,4-naphthoquinone

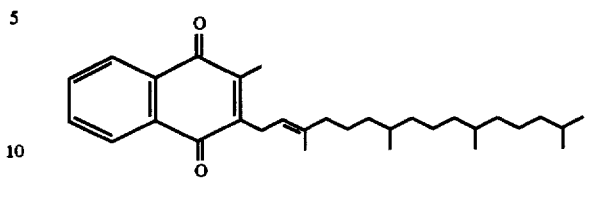

In toluene (25 ml), were dissolved 4.6 g (8.9 mmol) of 1,4,4$_a$,9$_a$-tetrahydro-9$_a$α-methyl-4$_a$α-[(2E')-3',7',11',15'-tetramethyl-2'-hexadecaenyl)-1α,4α-methanoanthraquinone, thereby conducting a Retro Diels-Alder reaction and post-treatment in the same manner as in Example 2 to obtain 3.9 g of the title compound as a yellow oil (yield: 97%, HPLC purity: 99.6%).

This product consisted with a standard sample in TLC, HPLC and capillary GC.

What is claimed is:

1. A 1,4,4$_a$,8$_a$-tetrahydro-4$_a$α-alkenyl-1α,4α-methanonaphthalene-5,8-dione derivative represented by the following formula (I):

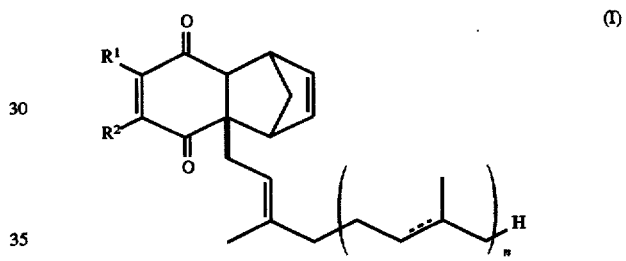

wherein R$^1$ and R$^2$ are identical with or different from each other and are a lower alkyl or lower alkoxy group, or together form an aromatic ring, n stands for 0 or an integer of 1–9, and a linkage $=\!=\!=$ is a single or double bond.

2. The 1,4,4$_a$,8$_a$-tetrahydro-4$_a$α-alkenyl-1α,4α-methanonaphthalene-5,8-dione derivative (I) as claimed in claim 1 which is one selected from 1,4,4$_a$,9$_a$-tetrahydro-4$_a$α-(3'-methyl-2'-butenyl)-1α,4α-methanoanthraquinone; 1,4,4$_a$,9$_a$-tetrahydro-4$_a$α-(3',7'-dimethyl-2',6'-octadienyl)-1α,4α-methanoanthraquinone; 1,4,4$_a$,9$_a$-tetrahydro-4$_a$α-(3',7',11'-trimethyl-2',6',10'-dodecatrienyl)-1α,4α-methanoanthraquinone; 1,4,4$_a$,9$_a$-tetrahydro-4α-(3',7',11',15'-tetramethyl-2',6',10',14'-hexadecatetraenyl)-1α,4α-methanoanthraquinone; 1,4,4$_a$,9$_a$-tetrahydro-4$_a$α-(3',7',11',15',19'-pentamethyl-2',6',10',14',18'-eicosadecaheptaenyl)-1α,4α-methanoanthraquinone; 1,4,4$_a$,9$_a$-tetrahydro-4$_a$α-(3',7',11',15'-tetramethyl-2'-hexadecaenyl)-1α,4α-methanoanthraquinone; and 1,4,4$_a$,8$_a$-tetrahydro-6,7-dimethoxy-4$_a$α-solanesyl-1α,4α-methanonaphthalene-5,8-dione.

\* \* \* \* \*